United States Patent [19]

Stein et al.

[11] Patent Number: 5,394,506
[45] Date of Patent: Feb. 28, 1995

[54] FRAGRANCE DISPENSER FOR AN AUTOMOBILE

[76] Inventors: Robert D. Stein; Sherry B. Gunsberger, both of 515 N. Highlands Dr., Hollywood, Fla. 33021

[21] Appl. No.: 57,121

[22] Filed: May 3, 1993

[51] Int. Cl.[6] ............ F24F 6/10; F22B 1/28
[52] U.S. Cl. ............ 392/395; 392/390; 219/202
[58] Field of Search ........ 392/392, 390, 386, 395; 219/202; 261/142, DIG. 65

[56] References Cited

U.S. PATENT DOCUMENTS

| D. 306,644 | 3/1990 | Luthy | 219/386 X |
|---|---|---|---|
| 2,849,606 | 7/1989 | Martens et al. | 392/392 X |
| 2,898,649 | 8/1959 | Murray | 392/395 X |
| 3,006,042 | 10/1961 | Calandra | 392/386 X |
| 3,551,092 | 12/1970 | Masson | 392/386 |
| 3,872,280 | 3/1975 | Van Dalen | 392/390 |
| 4,214,146 | 7/1980 | Schimanski | 392/390 |
| 4,251,714 | 2/1981 | Zobele | 392/395 |
| 4,391,781 | 7/1983 | Van Lit | 392/390 X |
| 4,574,181 | 3/1986 | Spector | 392/390 |
| 4,604,245 | 8/1986 | Gutierrez | 261/DIG. 65 |
| 4,686,353 | 8/1987 | Spector | 392/390 |
| 4,692,590 | 9/1987 | Spector | 392/390 |
| 4,714,984 | 12/1987 | Spector | 362/226 |
| 4,725,712 | 2/1988 | Schroeder | 392/390 |
| 4,731,521 | 3/1988 | Spector et al. | 392/390 |
| 4,808,347 | 2/1989 | Dawn | 261/DIG. 65 |
| 4,968,456 | 11/1990 | Muderlak et al. | 261/DIG. 65 |

FOREIGN PATENT DOCUMENTS

| 2626452 | 8/1989 | France | 392/405 |
|---|---|---|---|
| 55-23853 | 2/1980 | Japan | 219/202 |
| 63-282421 | 11/1988 | Japan | 392/386 |
| 2062199 | 5/1981 | United Kingdom | 392/390 |
| 2211415 | 7/1989 | United Kingdom | 392/390 |

*Primary Examiner*—Teresa J. Walberg
*Attorney, Agent, or Firm*—Malin, Haley, DiMaggio & Crosby

[57] ABSTRACT

A fragrance dispenser for a vehicle, such as an automobile, that utilizes the automobile's cigarette lighter as a heating source. The fragrance dispenser includes a housing for plugging it into the cigarette lighter socket and a wedge-shaped divergent housing that has an open, or mostly open, top portion that allows for dispensing of the fragrance, while at the same time providing visual inspection of the remaining material. The system utilizes a replaceable cartridge of a volatile fragrance emitting material.

5 Claims, 1 Drawing Sheet

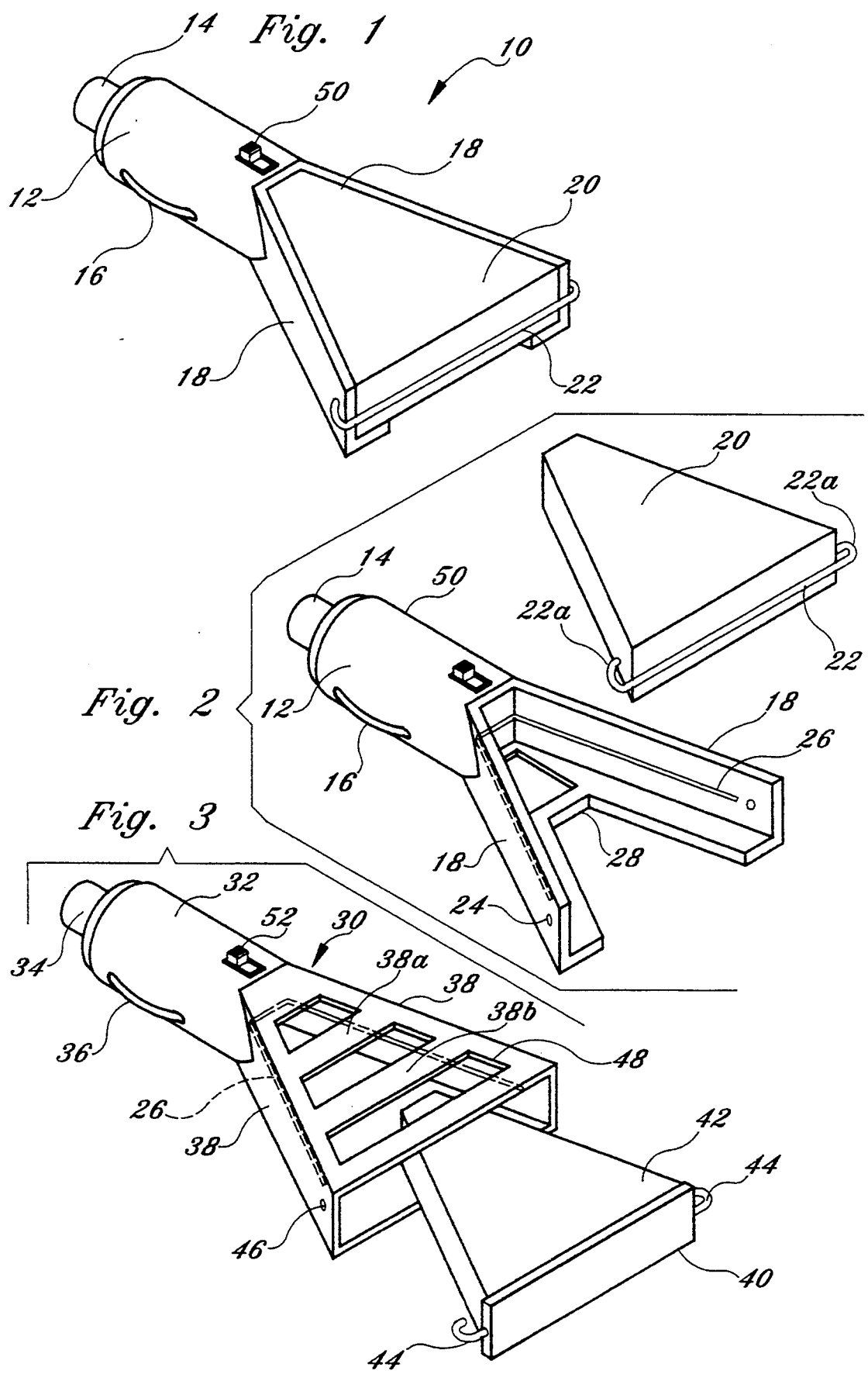

FRAGRANCE DISPENSER FOR AN AUTOMOBILE

BACKGROUND OF THE INVENTION

1. Field of the Invention

This invention relates to a device for dispensing fragrance or aroma in an automobile or boat using the cigarette lighter socket of the automobile for heating the fragrance producing material, and in particular, to a fragrance producing device for use in an automobile that includes a replaceable fragrance material cartridge that is readily observable when it is time to replace the cartridge after the material is expended.

2. Description of the Prior Art

The use of air fresheners, air fragrance dispensing devices, and aromatic devices is well known in many environments. Devices are known for providing a fragrance within an automobile. U.S. Pat. Des. No. 306,644, issued to Latley Mar. 13, 1990, shows an electronic fragrance dispenser for insertion into an automobile cigarette lighter socket.

U.S. Pat. No. 5,060,864, issued to Nishi et al. Oct. 29, 1991, shows a perfume emitting device for use in an automobile. The Nishi et al. device shows a liquid dispenser that is atomized under pressure carried in a tank located in the vehicle. U.S. Pat. Des. No. 306,644 is a small, portable device that is inserted into a cigarette lighter. One of the drawbacks of the Design Patent item is that, because of the total enclosure of the fragrance, it is impossible to determine the amount of material expended without disassembling the entire device.

U.S. Pat. No. 4,814,212, issued to Spector Mar. 21, 1989, shows an automobile air freshener unit that employs a plurality of thin films, a display object, and pressure sensitive adhesive to attach the thin film to a window. An outer film has a fragrance dispensing layer of a volatile fragrance.

The present invention provides for a reusable cartridge replacement for use in a fragrance dispenser that is heated through the use of the cigarette lighter socket, which allows for periodic or continuous fragrance dispensing, while at the same time allowing the user to readily and visually determine instantaneously whether or not the cartridge has expended the fragrance material. The device also provides for readily replaceable cartridges which can be quickly inserted into the device for replenishment of the fragrance-enhancing material.

SUMMARY OF THE INVENTION

A fragrance dispenser that utilizes a heated element for dispensing a material that includes a fragrance for enhancing and freshening the air, particularly in a vehicle, such as an automobile or truck. The device includes a housing, a pair of electrical contacts connected to the housing, with the portion of the housing being cylindrically shaped and sized for fitting into the female socket of a typical vehicle cigarette lighter for receiving an electrical current from the cigarette lighter system, and a fragrance material storage chamber that includes heated electrical elements that are placed near or in contact with a cartridge containing a fragrance emitting material that is especially active when heated. The device may or may not include an on/off switch, depending on the utilization of the device, or a spring loaded position that can be inserted farther into the electrical socket for a temporary or instantaneous heating period which then, upon reaching a certain temperature, pops outwardly, disengaging the electrical contact and turning off the power to the heating units.

The fragrance emitting material, which includes typically a wax-like base containing a volatile or aromatic chemical, is typically shaped and sized in a cartridge form to fit snugly within the fragrance material receiving chamber of the overall housing. In a typical embodiment, the fragrance material may be a truncated trapezoid or wedge-shaped cartridge that includes at one side a wall made of the same material as the housing to allow the device to be snapped into place for use.

The cartridge includes a separate housing that holds the replacement cartridges of fragrance dispensing material and that snaps, in one embodiment, into the basic housing of the overall heated dispenser itself.

The actual material or chemicals used in the fragrance dispensing material could be that which is commercially available for household-type air freshener and dispensers that come in a solid form and are heated for enhancing the action of the fragrance.

In one embodiment, heating strips may be included which are insulated wires that permit heat transfer along the housing that holds the cartridge to the material to allow heating of the material which rapidly accelerates the fragrance dispensing properties of the unit.

The housing that holds the fragrance material cartridge includes a plurality of large, open slots or apertures which, while rigidly holding onto the fragrance enhancing material, allow one to instantaneously visually ascertain that the fragrance dispensing material is almost completely used up.

In accordance with these and other objects which will be apparent hereinafter, the instant invention will now become described with particular reference to the accompanying drawings.

BRIEF DESCRIPTION OF THE DRAWINGS

FIG. 1 shows a perspective view of the present invention's preferred embodiment.

FIG. 2 shows an exploded view of the invention as shown in FIG. 1.

FIG. 3 shows an exploded view of an alternate embodiment of the preferred invention.

DESCRIPTION OF THE PREFERRED EMBODIMENT

Referring now to the drawings, and in particular FIG. 1, the present invention is shown generally at 10, comprised of a cylindrical rigid body 12 that has an electrical contact 14 and a separate electrical contact 16 that cooperate and provide on the inside sufficient electrical circuitry to act as a heating element when plugged into a conventional automobile cigarette lighter that typically operates off a 12-volt system. A rigid, L-shaped pair of walls 18 are firmly attached to the cylindrical housing 12 and receive a volatile fragrance emitting substance 20 which is trapezoidally shaped to fit within the L-shaped walls 18, leaving an open trapezoidal shaped upper surface. A rigid bar 22 is affixed firmly to the volatile fragrance emitting substance 20 and allows it to be attached to the diverging walls 18 so that the fragrance emitting substance 20 cannot fall out or accidentally be removed from its contact position within the L-shaped walls 18, where it fits snugly.

Referring now to FIG. 2, the invention is shown with the volatile fragrance emitting substance 20 in a position away from the L-shaped walls 18, which include on each side a small indentation 24 that is sized and shaped to receive clip ends 22a at the end of rigid bar 22 so that the entire unit comprising the rigid bar 22 and volatile fragrance emitting material 20 fit snugly and remain in place once snapped in place in view of the indentations 24. In effect, the indentations 24, one on each side on the outside of L-shaped wall 18, and the protruding members 22a, act as a fastener to hold the fragrance emitting material 20 in place. Note that on the inside of each L-shaped wall 18 are electric heating elements 26, one on each side, which are connected electrically to the circuit and to contacts 14 and 16 which are received into the automobile cigarette lighter for heating wire 26 which acts to heat a volatile fragrance emitting substance 20. The consistency of the volatile fragrance emitting substance 20 is such that it is a waxlike material that, when heated, acts to readily evaporate an alcohol-based fragrance such as terpene-based fragrance. This would be a suitable volatile material for dispensing from the device.

To operate the device, the wedge-shaped removable and replaceable cartridge 20, that is in fact the volatile fragrance dispensing material, is inserted into the housing between the L-shaped legs 18 and it is snapped in place. Once in place, the entire cylindrical housing unit can then be pushed into a conventional cigarette lighter where the power from the automobile's electrical system will provide heat energy to the heating element 26. In addition, an electrical switch 50 could be employed, which allows one to turn the heating element on or off when the device is plugged into the vehicle's cigarette lighter, or the on/off may be provided such as is done for a cigarette lighter where, when a certain temperature is reached, the device will pop out and still remain in the socket of the vehicle cigarette lighter.

One of the advantages shown in FIGS. 1 and 2 is the complete openness of the volatile fragrance dispensing material 20 relative to its environment so that maximum air flow and air contact is achieved for dispensing the fragrance contained therein while at the same time, the user can readily observe the relative amount of fragrance dispensing material left so that it is simple to determine when the cartridge itself of fragrance material must be replaced.

FIG. 3 shows an alternate embodiment of the invention, wherein it has a similar cylindrical housing 32, electrical contact 34, electrical contact 36, and a heating element 48 as described above. In addition, the housing is different in that it incudes diverging walls 38 that are enclosed on the top and bottom and include crossover connecting bars 38a and 38b, making the entire housing connected together. This forms an enclosure, but still provides three openings on the top that permit both visual inspection of the material retained and openings to allow the fragrance to escape through the top of the housing. The fragrance dispensing material 42, which is similar to that shown above as fragrance material 20, in this embodiment includes a solid wall 40 which is firmly attached to the fragrance emitting material 42 and includes snaps or fasteners 44. The fasteners 44, which are small wedge-shaped arms, are flexible enough to move in and out of detents 46 on the outside walls of walls 38 so that the entire fragrance emitting material 42 and the back protective wall 40 will fit snugly within the trapezoidal shaped housing of the device. Again, the heating operation is similar to that described above. In this particular embodiment, there is additional structure to prevent breakup or segments of the fragrance emitting material from falling out of the unit, while at the same time providing sufficient large openings at the top for visual inspection and complete transfer of fragrance into the ambient atmosphere.

The primary purpose of the invention as disclosed provides for efficient transfer of fragrance to the ambient atmosphere while at the same time allowing a replaceable cartridge to be used and a continuous, readily visual display of the remaining volatile fragrance emitting material in each embodiment. As shown in FIG. 3, an on/off switch 52 may also be employed.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A fragrance dispensing device for use in an automobile or other similar type vehicle for dispensing fragrance through the use of the automobile cigarette lighter socket which is electrically connected to the automobile electrical power source battery, said fragrance dispensing device comprising:

a first cylindrical housing sized and shaped to be received into a conventional automobile lighter socket;

circuit means connected to and in said cylindrical housing and adapted to cooperate with circuit elements in the lighter socket for providing current;

heating element means connected to said circuit means for providing heat;

a second housing which includes a pair of diverging walls, each wall having a lower lip portion, said walls supporting a trapezoidal-shaped body;

a volatile fragrance dispensing material shaped in a trapezoidal shaped body and sized to fit into and between said diverging walls; and means for retaining said volatile fragrance dispensing material body between said diverging walls, whereby said diverging walls define a space with a totally open top for dispensing said fragrance while said heating elements means is activated and allowing for visual observation of the remaining amount of material.

2. A device as in claim 1, wherein said retaining means includes a bar connected to said fragrance material and a pair of fasteners at the end of the bar for connection to said diverging walls.

3. A device as in claim 1, including means for switching said heating element on and off, connected to said cylindrical housing and said electrical circuit.

4. A device as in claim 1, wherein said diverging walls include a plurality of braces which attach along the top portion of said diverging walls for escape of said fragrance material.

5. A device as in claim 4, including an end retaining wall connected to said fragrance material, said end retaining wall and said divergent walls both including corresponding fasteners for securing the fragrance dispensing material and said end retaining wall within said diverging walls.

* * * * *